United States Patent [19]

Nakatani

[11] Patent Number: 5,448,504
[45] Date of Patent: Sep. 5, 1995

[54] APPARATUS FOR THERMAL ANALYSIS

[75] Inventor: Rintaro Nakatani, Tokyo, Japan

[73] Assignee: Seiko Instruments Inc., Tokyo, Japan

[21] Appl. No.: 65,054

[22] Filed: May 24, 1993

[30] Foreign Application Priority Data

May 22, 1992 [JP] Japan .................................. 4-131075

[51] Int. Cl.⁶ ............................................. G01K 17/06
[52] U.S. Cl. ........................................ 364/557; 165/1;
165/13; 165/18; 340/655
[58] Field of Search ........................ 364/557; 165/1, 13,
165/18; 340/655

*Primary Examiner*—Emanuel T. Voeltz
*Assistant Examiner*—Thomas Peeso
*Attorney, Agent, or Firm*—Spensley Horn Jubas & Lubitz

[57] ABSTRACT

A CPU 8 computes differential data of thermal analysis data in a data memory 9a, stores the differential data in a differential data memory 9b, scans secondary differential data, and detects the crossing point of a set differential width as a peak point. The CPU 8 computes second differential data, stores the data in a second differential data memory 9c, scans the second differential data, detects then as a stable area when a part within a set second differential width continues as for as over a set length and the corresponding thermal analysis data has a certain gradient or less. The scanning of the differential data is performed to detect the peak of the differential data as the maximum gradient point. Computation of the transition point and heat of transition having made a peak point, stable area, and maximum gradient point as specified points is performed, and the results are outputted to a CRT 7 or the like.

14 Claims, 13 Drawing Sheets

20a THERMOANALYSIS DATA

20b DIFFERNTIAL DATA
PEAK DETECTION DIFFERENTIAL WIDTH (LIMIT)
PEAK DETECTION DIFFERENTIAL WIDTH (START)

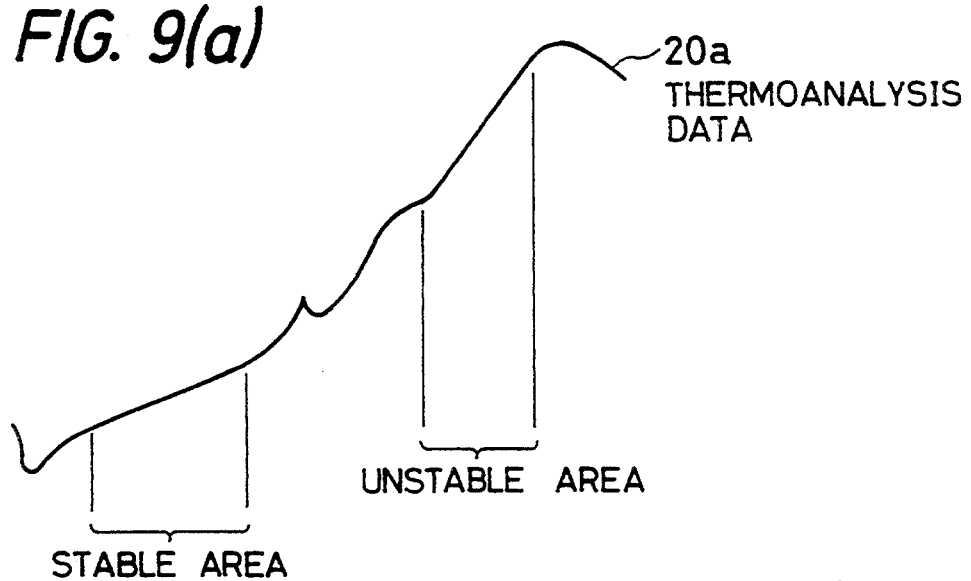
FIG. 9(a)
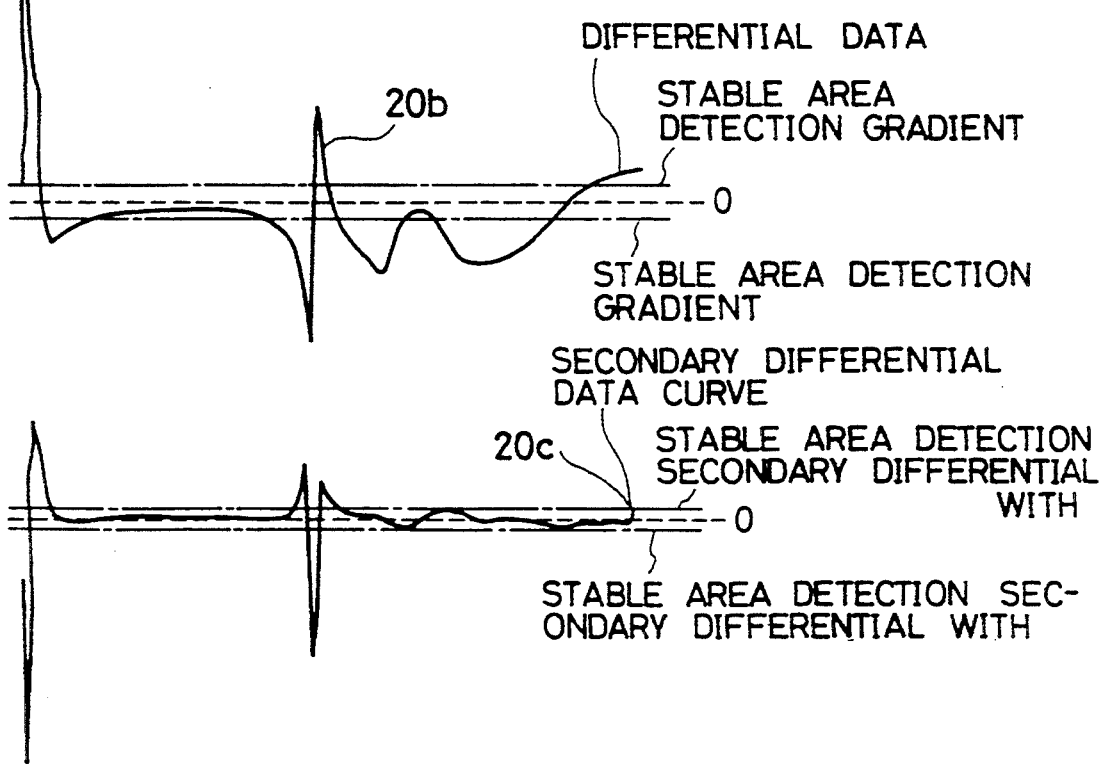
FIG. 9(b)
FIG. 9(c)

FIG. 13

《DSC ANALYSIS》

〈DSC READ〉
NO. TEMP
[C]
1  251.25
2  161.59

〈DSC DELTA H〉
NO. DELTA H
[MJ/MG]
1   3.98807E+01
2  -3.86082E+01

〈DSC TT〉
NO TEMP
[C]
1  236.5
2  260.15
3  147.22
4  172.55

APPARATUS FOR THERMAL ANALYSIS

BACKGROUND OF THE INVENTION

The present invention relates to a thermoanalysis arrangement.

Analysis of thermoanalysis data is performed by obtaining a peak point, a transition point, and the heat of transition from a waveform derived from data. Conventionally, in these operation, users have visually specified a point on the data waveform and a thermoanalysis arrangement has computed the transition point or the like based on the specified point. To obtain the heat of transition, for example, the data waveform is traced to the right and left from the peak point, as recognized by the user, two points recognized as delimiting a stable area (point where data change is not recognized) by the user are transferred to the thermoanalysis arrangement, and the thermoanalysis arrangement computes the heat of transition by using the two points. In addition, to obtain the transition point, the data waveform is traced to either the right or left from the point recognized as the peak point by the user, a point recognized as a stable area by the user (point A) and a point recognized as the point at which the gradient is greatest (the maximum gradient point) between the point A and the peak point-(point B) are transferred to the thermoanalysis arrangement, and the thermoanalysis arrangement computes the transition point by using the two points.

However in the prior art, all recognition of the points used as a trigger for computation is done by the user. Therefore, there has been problems in that it takes a lot of time to analyze a large quantity of data, and the recognition of the points to be specified varies from one individual to another so that there is no reproduceability of the results.

The present invention is made to solve the above problems and its objects are power saving and speeding up when a large quantity of data are analyzed and improving of reproduceability and uniformity of analysis results.

SUMMARY OF THE INVENTION

The present invention is developed to solve the above problems.

The above and other objects are achieved, according to the present invention, by a thermoanalysis arrangement comprising:

a first data memory storing a plurality of thermoanalysis data values;

differentiating means connected to the first data memory for differentiating the thermoanalysis data values in the first data memory to compute a plurality of differential data values;

a differential data memory connected to the differentiating means for storing the differential data values;

point detecting means connected to the differential data memory for detecting a peak point on a curve formed by the differential data values where the curve crosses a preset peak detection differential width value corresponding to a peak thermoanalysis data value;

means connected to the point detecting means for outputting a representation of the detected peak point;

means for detecting stable areas of the curve;

means for detecting a maximum gradient point of the curve;

means for computing an intersection point between a function approximating the thermoanalysis data on all or a part of the detected stable areas and a function approximating the thermoanalysis data at the maximum gradient point as a transition point;

means for computing heat of transition between two detected stable areas enclosing the detected peak point; and means for outputting the computed transition point and heat of transition.

The function of the above arrangement is: at first, a sample is heated in a heating furnace controlled by a measuring controller under the control of the temperature program of the measuring controller, the temperature of the sample or the temperature in the vicinity of the sample is detected by the temperature sensor, a physical quantity, or characteristic, of the sample which changes in dependence on the temperature change of the sample is detected by the physical quantity sensor, the detected temperature and the detected physical quantity are digitized by the measuring and control section, and digitized data is stored in the data memory by the means for storing digitized data in the data memory.

Differential data is computed from the stored data by the means for computing differential data and stored in the differential data memory to detect the peak point by the means for detecting a peak point. At this time, the peak detection differential width inputted to the detection level memory is referenced by the means for inputting detection levels, After the peak point is detected, secondary, or second, differential data is computed by the means for computing secondary differential data to store the data in the secondary, or second, differential data memory and stable areas are detected by the means for detecting stable areas. At this time, the stable area detection secondary differential width, stable area detection length and stable area detection gradient inputted to the detection level memory are referenced by the means for detecting detection levels. After stable areas are detected, the maximum gradient point is detected by the means for detecting the maximum gradient points. At this time, the maximum gradient detection differential width inputted to the detection level memory is referenced by the means for inputting detection levels.

After the peak point, stable areas and maximum gradient point are detected, they are referenced to compute the transition point by the means for computing transition points, and after the heat of transition is computed by the means for computing heat of transition, outputting of the peak point, transition point and heat of transition is achieved by the means for outputting the peak points, transition points and heat of transition.

BRIEF DESCRIPTION OF DRAWINGS

FIGS. 9(a), 9(b) and (c) are explanatory views of the stable area detection gradient on the stable area detection method of the present invention.

FIG. 13 is an example of numerical information output by the printer of the embodiment of FIG. 1.

DESCRIPTION OF THE PREFERRED EMBODIMENTS

A preferred embodiment of the present invention is described below with reference to the drawings.

Figure 1:
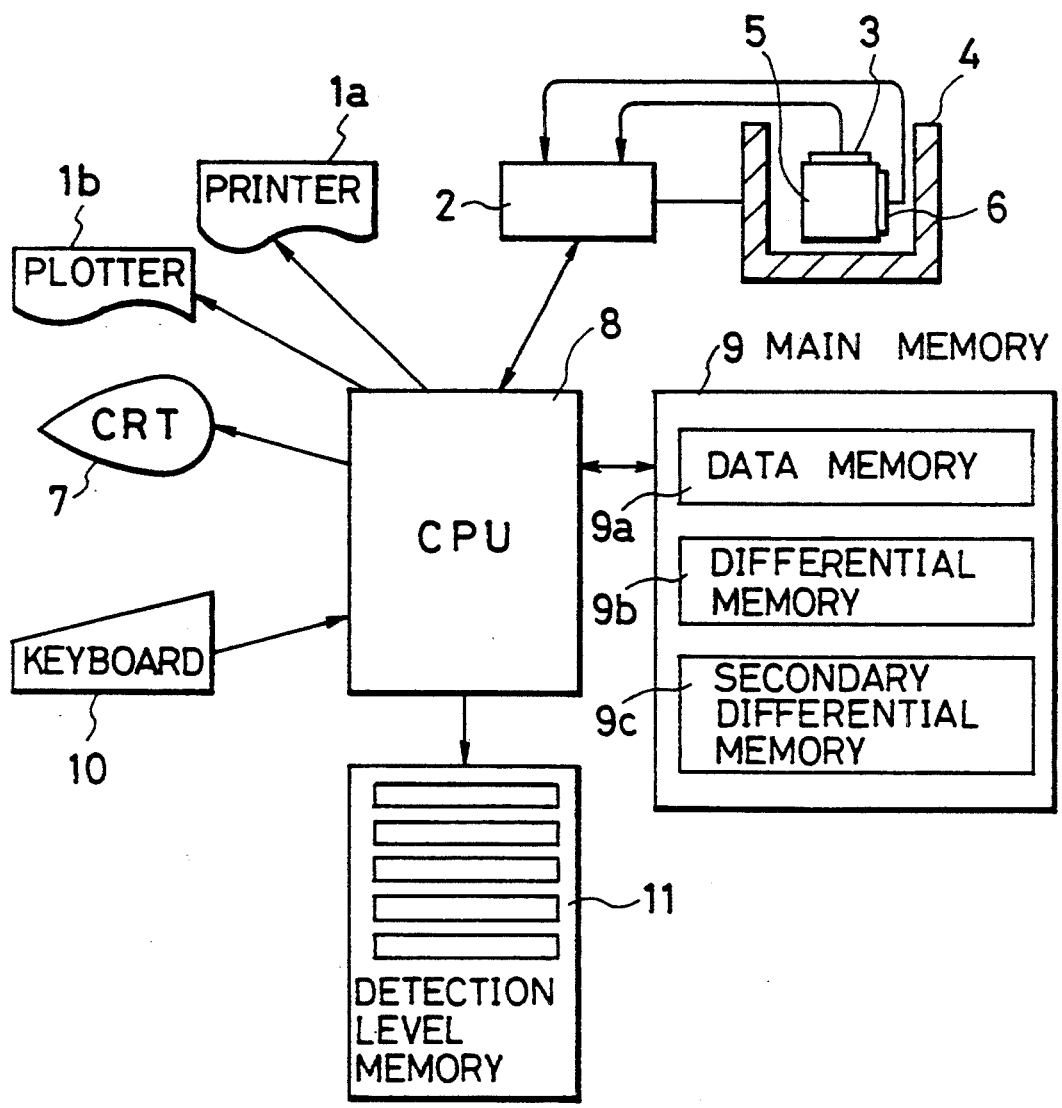
FIG. 1 is a block diagram showing a preferred embodiment of the present invention.

FIG. 1 shows a heating furnace 4 into which a user has previously put a sample 5 to be measured. The user intentionally inputs information, necessary for measurements, of a temperature program and the like by using a CRT 7 controlled by a CPU 8 and a keyboard 10. The information necessary for measurements is transferred to a measurement controller 2 through the CPU 8 and the measurement is started.

The measurement controller 2 comprises a temperature controller and temperature sensor 3 for controlling the heating furnace, an A-D converter for digitizing signals sent from a physical value sensor 6, and a microprocessor for exchanging information with the CPU 8 by controlling the A-D converter and the like. For this embodiment, a microprocessor is built into the measurement controller 2. However, a method can be used in which the CPU 8 directly controls the temperature controller and A-D converter without using the microprocessor.

When a command for starting measurement is transferred to the measurement controller 2 from the CPU 8, the measurement controller 2 controls the heating furnace 4 according to the temperature program, detects a physical quantity change dependent on the temperature change of the sample 5 with the physical quantity sensor 6, and digitizes the value to transfer the digitized data to the CPU 8. The CPU 8 stores the data in the data memory 9a of the main memory 9.

Before starting analysis, the user inputs the information necessary for analysis, including detection and the like (peak detection differential width [start, limit], stable area detection secondary differential width [start, limit], stable area detection length, stable area detection gradient, and maximum gradient point detection differential width [start, limit]) by using the CRT 7 and keyboard 10 similarly to the case of measurement. Various analyses for thermal analysis data become possible with different combinations of information items.

Figure 2:
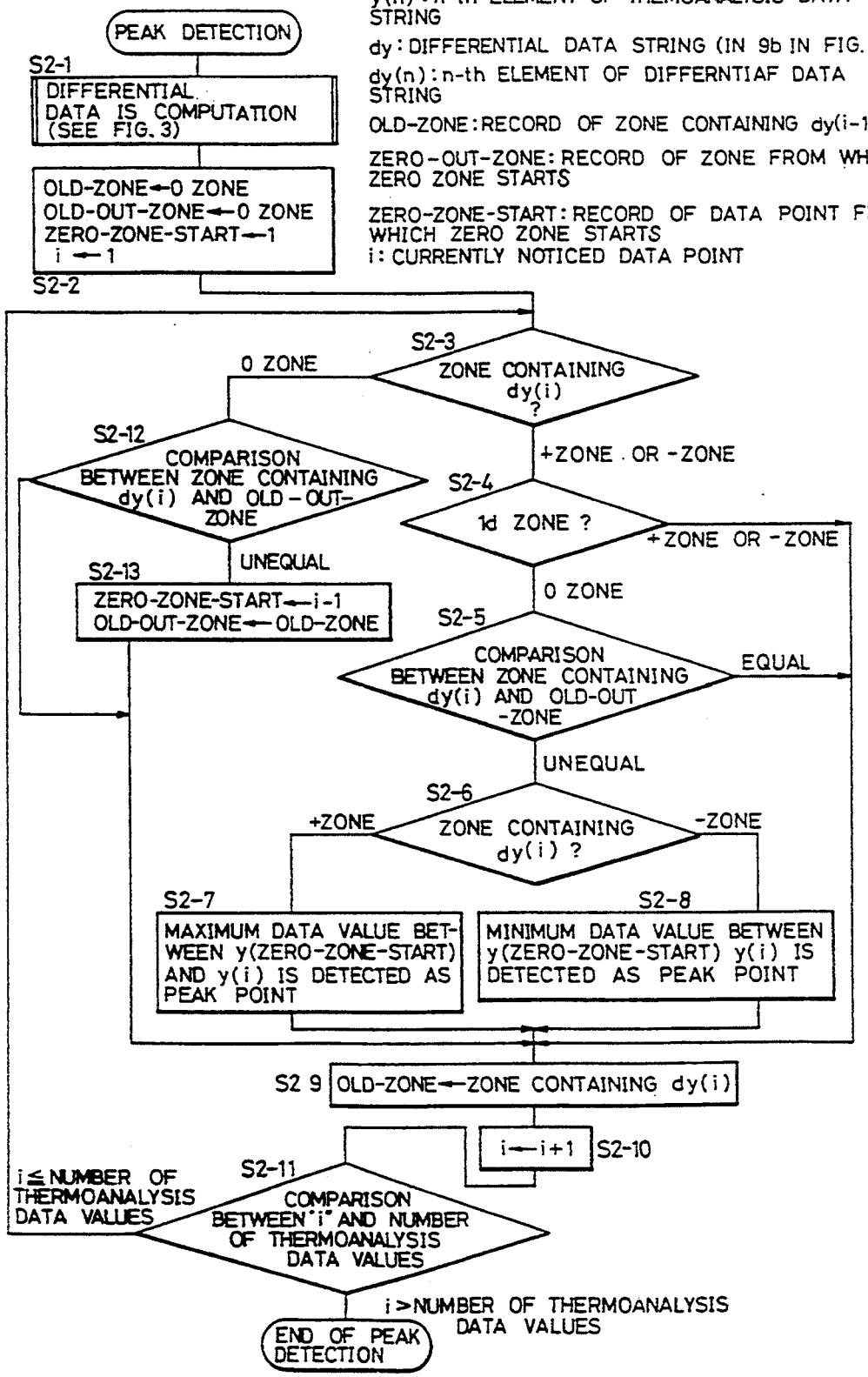
FIG. 2 is a flow chart showing the peak detection method of the present invention.
Figure 3:
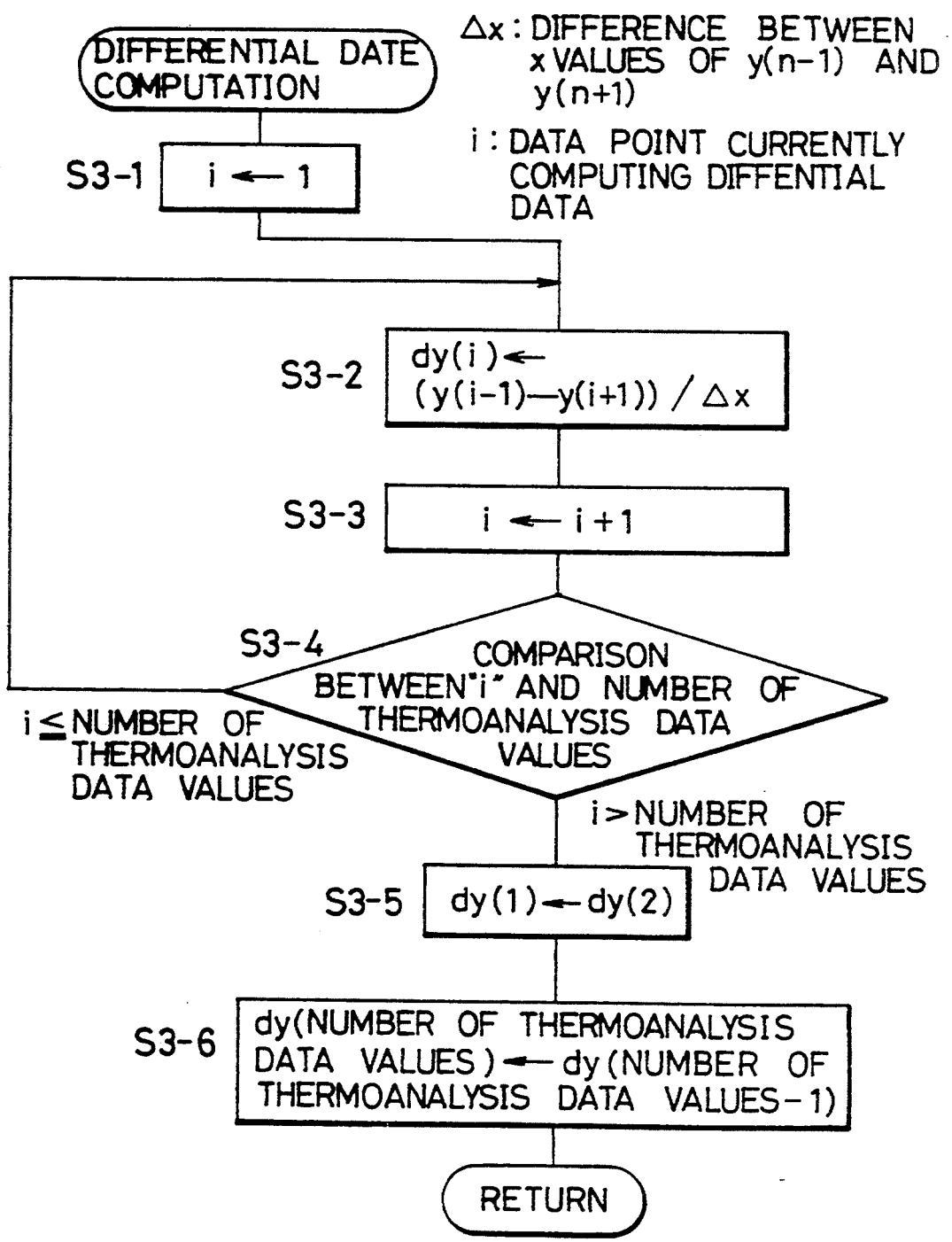
FIG. 3 is a flow chart showing the differential computation method of the present invention.

When analysis is started, the CPU 8 performs the detection of the peak point by the operation shown in the flow charts of FIGS. 2 and 3. This operation will be explained by referring to FIGS. 2, 3, and 4.

First, the CPU 8 calls a subroutine for computing differential data from the thermal analysis data in the data memory 9a (S2-1). FIG. 3 shows the subroutine for computing differential data. Data except for the first and last differential data values is computed by the following formula (S3-1 to S3-4).

$$dy(i) = \{y(i-1) - y(i+1)\}/\Delta x$$

where, dy(i): i-th differential data (in the differential data memory 9)

y(i−1): (i−1)-th thermal analysis data (in the data memory 9a)

Δx: difference between x values of y(i−1) and y(i+1).

In FIGS. 4, 5, 8, 9, 11 and 12, y is the coordinate in the vertical direction and corresponds to the sample characteristic being measured and x is the coordinate in the horizontal direction and corresponds to the sample temperature.

The differential data string for the next following data point is used for the first differential data string (S3-5) and the differential data string for the point one ahead is used for the last differential data string (S3-6).

Figure 4A:
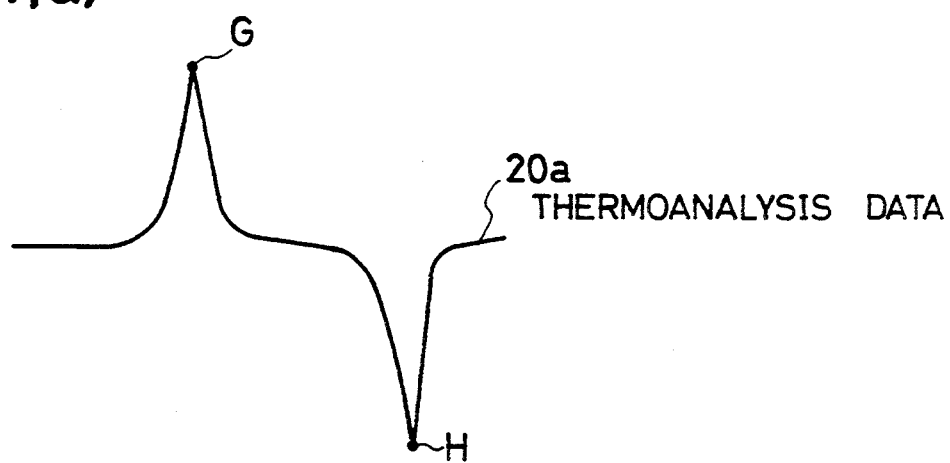
FIGS. 4(a) and (b) are explanatory views of the peak detection method of the present invention.
Figure 4B:
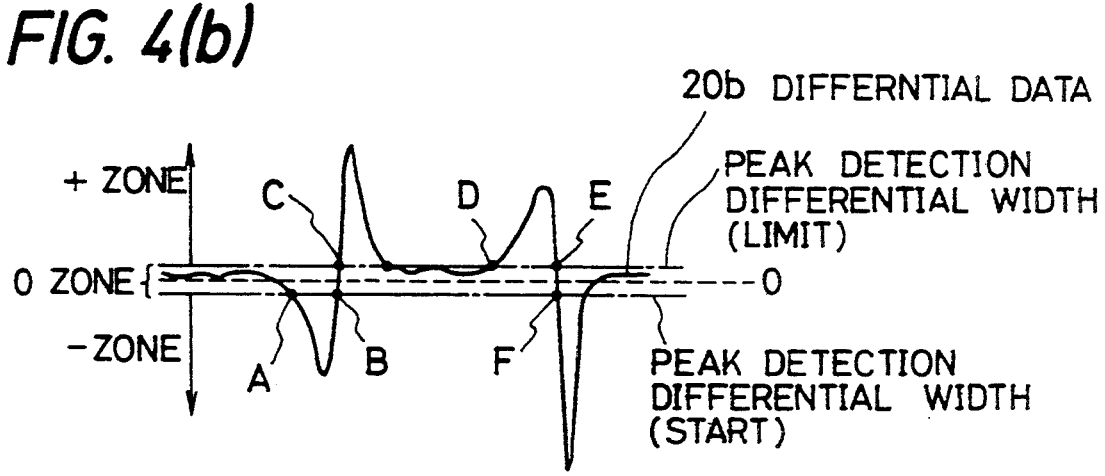

In the state where differential data is stored in the differential data memory 9, the CPU 8 scans the differential data to detect the peak point. As shown in FIGS. 4, the thermal analysis data curve 20a, FIG. 4(a), is differentiated and the differential curve 20b curve, FIG. 4(b), is obtained. The differential data curve 20b extends across three zones divided by values for the peak detection differential width [start] and peak detection differential width [limit] stored in the detection level memory 11. In this case, in the differential data curve 20b, larger values than the peak detection differential width [limit] are sorted into a + zone, those under the peak detection differential width [limit] and over the peak detection differential width [start] are sorted into a zero (0) zone, and those smaller than the peak detection differential width [start] are sorted into − zone. In this case, though zone division is performed with two parameters, the peak detection differential width [start] and the peak detection differential width [limit], it is also possible to divide zones by ± the peak detection differential width in which zero forms a center value.

Then, the zone containing "dy(i−1)" (old-zone), the fact that the data has entered into the zero zone from a previous zone (old-out-zone), and the fact that zero zone has started from a data point (zero-zone-start) are stored according to each differential data. After the initialization of variables is performed (S2-2), each differential data string is checked.

The zone containing the differential data of the point to be currently-noticed is checked (S2-3), and when it is the zero zone, it is checked if there is a change between the zone which existed for the differential data one ahead (S2-12). If there has been a change, it is considered that the crossing of the zero zone has started from the point to be currently-noticed (e.g. point B in FIG. 4). In this case, the point is recorded as the zero-zone starting point and the zone of the differential data one ahead (− zone with respect to the B point in FIG. 4) is also kept to be recorded (S2-13).

If the zone existing for the differential data of the point to be currently-noticed is not the zero zone, the zone which existed for the differential data value one ahead is checked (S2-4). If the zone is the zero zone, it is considered as the point where zero zone has ended (e.g. points C and D in FIG. 4). It is possible to know whether it crossed zero zone or not, that is, whether the peak has existed or not, by comparing the zone before entering the zero zone (zone stored in S2-13) with the zone of the point to be currently-noticed (S2-5). If it is the crossing end point of the zero zone (e.g. point C in FIG. 4), then both zones are not equal. If it is the point other than the crossing end point of zero zone (e.g. point D in FIG. 4), they are equal.

If the point to be currently-noticed is the crossing end point of zero zone, the zone of the point to be noticed is checked (S2-6). If it is the + zone, thermal analysis data corresponding to the region between the zero-zone starting point and the crossing end point is checked by assuming that a convex peak is present between the zero-zone starting point and the crossing end point. Among these points, the maximum point (point G in FIG. 4(a)) is detected as the peak point (S2-7). If it is the − zone, thermal analysis data corresponding to the region between the zero-zone starting point and the crossing end point is checked by assuming a concave peak is present between the zero-zone starting point and crossing end point. Among these points, the minimum point (point H in FIG. 4(a)) is detected as the peak point (S2-8).

When the processing steps S2-3 to S2-8 and S2-1 to S2-13 are completed, the zone of the point to be currently-noticed is stored as the zone one ahead (S2-9) and the point to be noticed is advanced by one point (S2-10) to detect the peak point by the process in which detection is performed the number of the current point, i.e. the value of i, and the number of thermal analysis data values (S2-11). When detection of the peak point is completed, the CPU 8 detects stable areas. This detection method includes the following two types.

Differential data is scanned and an area in which the points of differential data within the stable area detection differential width (peak detection differential width) continue as far as over the preset stable area detection length is detected as a stable area.

Differential data is differentiated to compute secondary differential data, the secondary differential data is scanned and an area in which the points of secondary differential data within the stable area detection secondary differential width continue as far as over the stable area detection length is detected as a stable area.

Figure 5A:
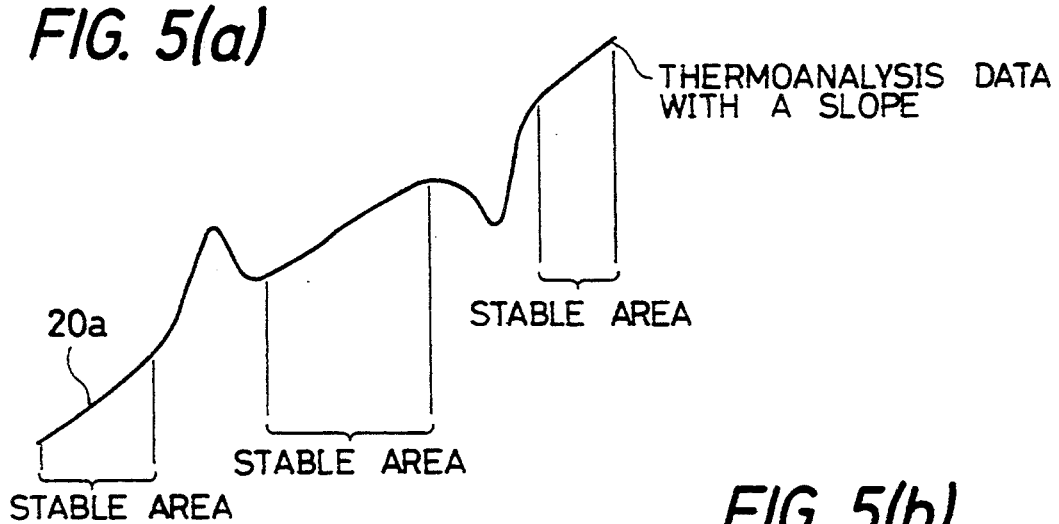
FIGS. 5(a), 5(b) and 5(c) are views for explaining the difference between the detection method according to differentiation of stable areas and the detection method according to secondary differentiation of the present invention.
Figure 5B:
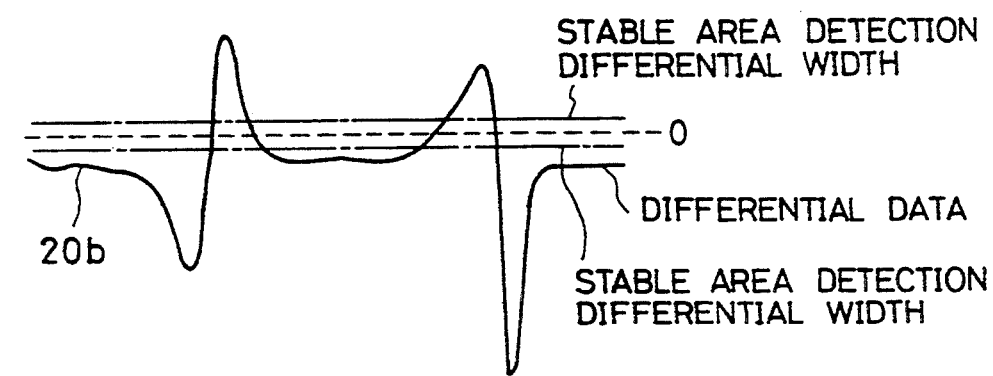
Figure 5C:
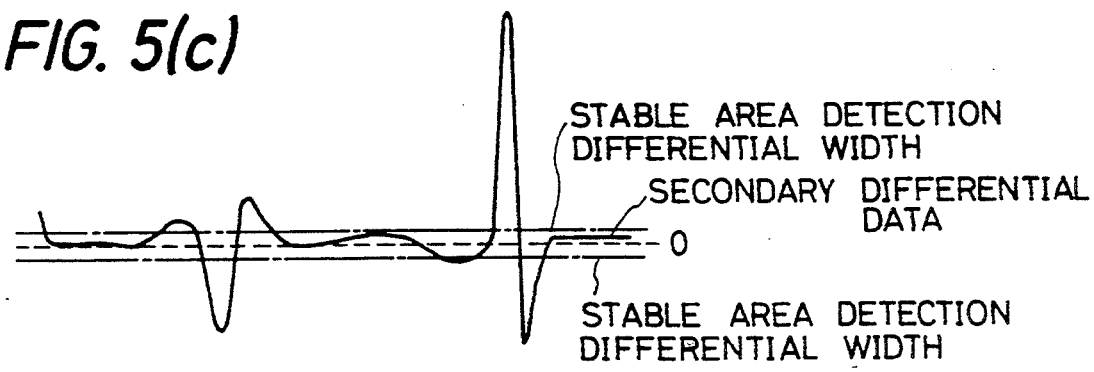

The former method presents a smaller computation load than does the latter one. However, when a stable area of the data with a slope such as those which are frequently seen in the data of DSC and the like among thermal analysis data is detected, it is frequently the case that the differential data of the area regarded as a stable area is not included within the stable area detection differential width, as in the case of the differential data curve 20b in FIG. 5(b). To avoid this, it is necessary to shift the stable area detection differential width by the former method or to detect a stable area by the latter method in which secondary differentiation is performed (FIGS. 5). This embodiment uses the latter method. The operation of the CPU 8 according to the latter method is described below with reference to FIGS. 6 to 9.

Figure 6:
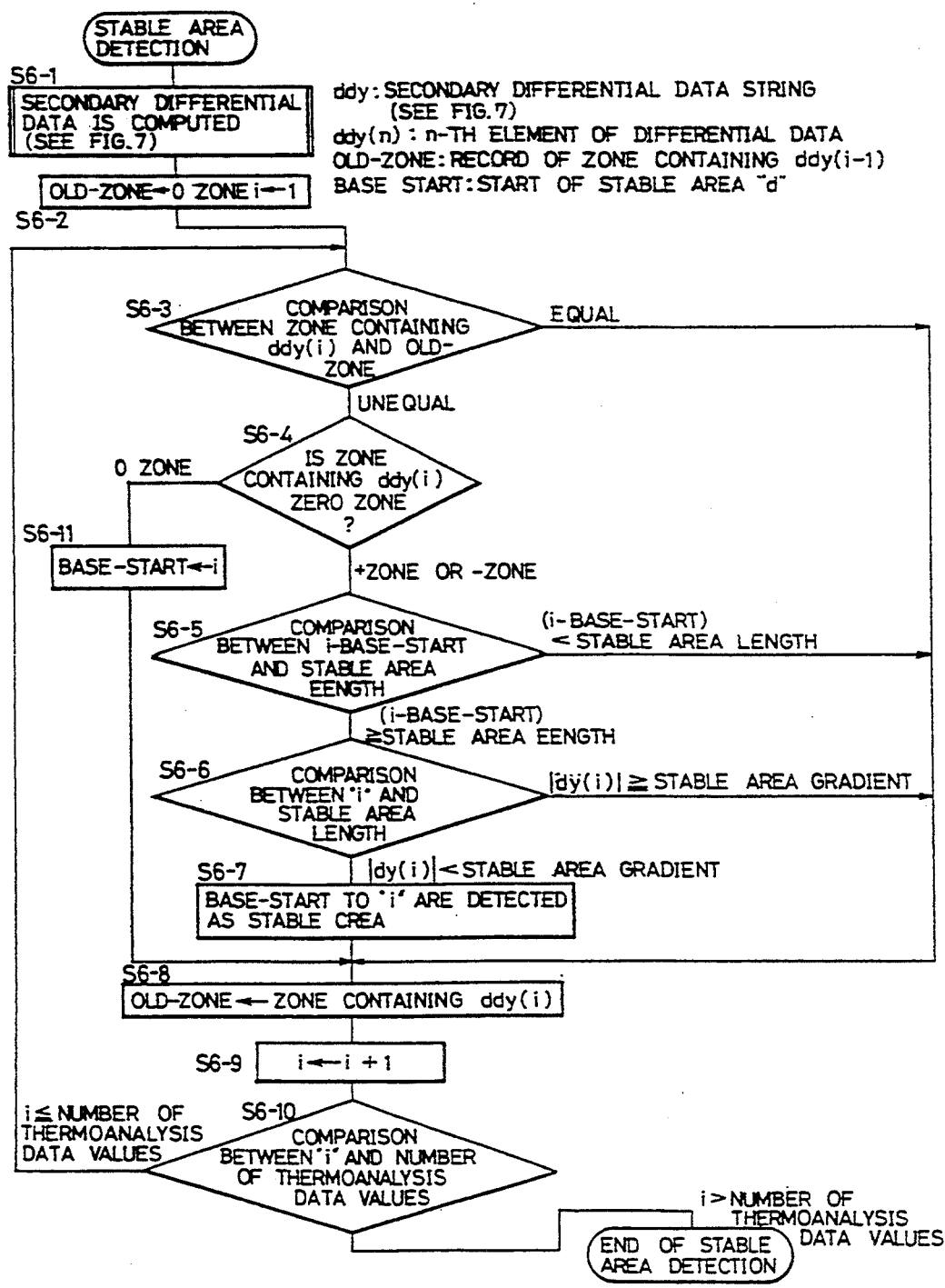
FIG. 6 is a flow chart showing the stable area detection method of the present invention.
Figure 7:
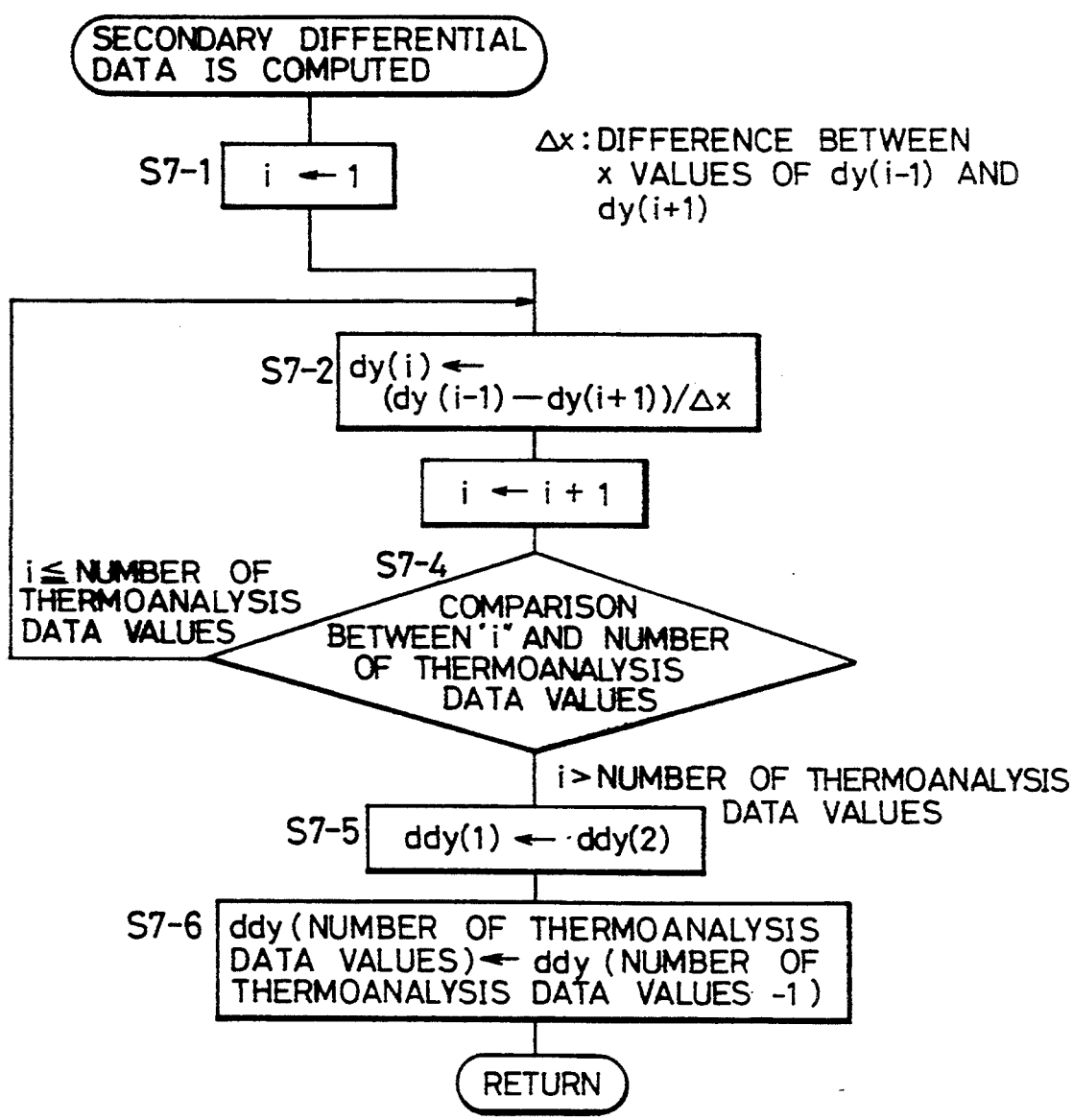
FIG. 7 is a flow chart showing the secondary differential computational method of the present invention.

The CPU 8 differentiates the differential data in the differential data memory 9b and accesses a subroutine for computing secondary differential data (FIG. 6, S6-1). FIG. 7 shows the subroutine for computing the secondary differential data. The data excluding the first and last values of the secondary differential data is computed by the following formula (S7-1 to S7-4).

$$ddy(i) = \{dy(i-1) - dy(i+1)\}/\Delta x$$

where,
ddy(i): i-th secondary differential data (in the secondary differential data memory 9c),
dy(i−1): (i−1)-th differential data (in the differential data memory 9b),
dy(i+1): (i+1)-th differential data (in the differential data memory 9b),
Δx: Difference between x values of dy(i−1) and dy(i+1).

The secondary differential data for one point after, or later, is put in for the first point of the secondary differential data (S7-5) and the double differential data one ahead, or earlier, is put in for the last of the secondary differential data (S7-6).

Figure 8A:
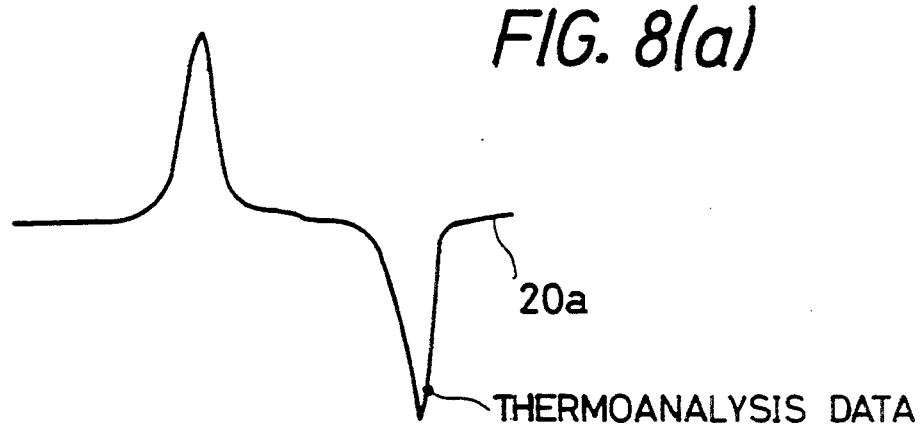
FIGS. 8(a) and 8(b) are explanatory views of the stable area detection method of the present invention.
Figure 8B:
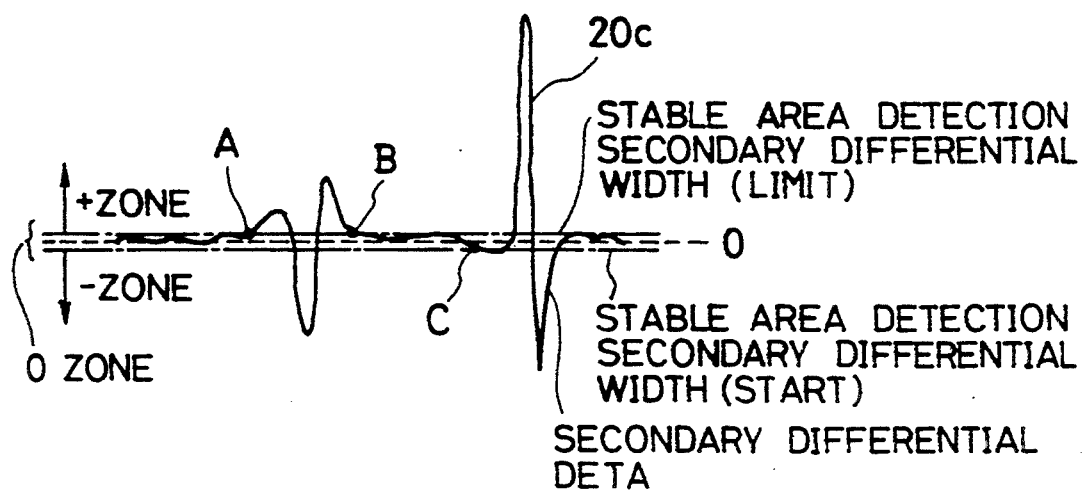

When secondary differential data is stored in the secondary differential data memory 9c, the CPU 8 scans the secondary differential data to detect stable areas. As shown in FIG. 8(b), the secondary differential data curve 20c exists in three zones divided by the stable area detection secondary differential width [start] and the stable area detection secondary differential width [limit] stored in the detection level memory 11. It is assumed that values larger than the stable area detection double differential width [limit] are in the + zone, those under the stable area detection secondary differential width [limit] and over the stable area detection secondary differential width [start] are in the zero zone, and those smaller than the stable area detection secondary differential width [start] are in the − zone. In this case, though zone division is performed with two parameters of the stable area detection secondary differential width [start] and the stable area detection secondary differential width [limit], it is also possible to divide the zones into ± stable area detection secondary differential width which use zero as the center.

After the initializations of necessary variables are performed, (S6-2), each secondary differential data is going to be checked. Then, the zone of the secondary differential data of the point to be currently noticed is compared with the zone of the secondary differential data one ahead (S6-3).

If there has been a change (e.g. points A, B, and c in FIG. 8(b)), the zone of the secondary differential data of the point to be currently-noticed is checked (S6-4). If the zone was the zero zone (e.g. point B in FIG. 8(b)), the point is recorded as a zero-zone starting point (S6-12). If not (e.g. points A and C in FIG. 8(b)), the length from the zero-zone starting point to this point is compared with the stable area detection length (S6-5). If the length from the zero-zone starting point to this point is longer than the stable area detection length, the absolute value of the differential data corresponding to this point is compared with the stable area detection gradient (S6-6).

In this comparison, there is a case where an unstable area is sometimes regarded as a stable area in the case of data with a slack slope which is frequently found in thermal analysis data, as in FIGS. 9. To prevent this, an operation is performed to eliminate data from the stable area when it has a gradient larger than that of thermal analysis data. For this embodiment, the operation is performed by comparing differential data with the stable area detection gradient. If the absolute value of the differential data is smaller than the stable area detection gradient, the area from the zero-zone starting point to this point is detected as a stable area (S6-7). When the processing S6-3 to S6-8 and S6-12 are completed, by using the processes in which the zone of the point to be currently noticed is stored as the zone one ahead (S6-8), the point to be noticed is advanced by one (S6-9) and the comparison is performed between the current value of i and the number of thermal analysis data, the stable area is detected.

Figure 10:
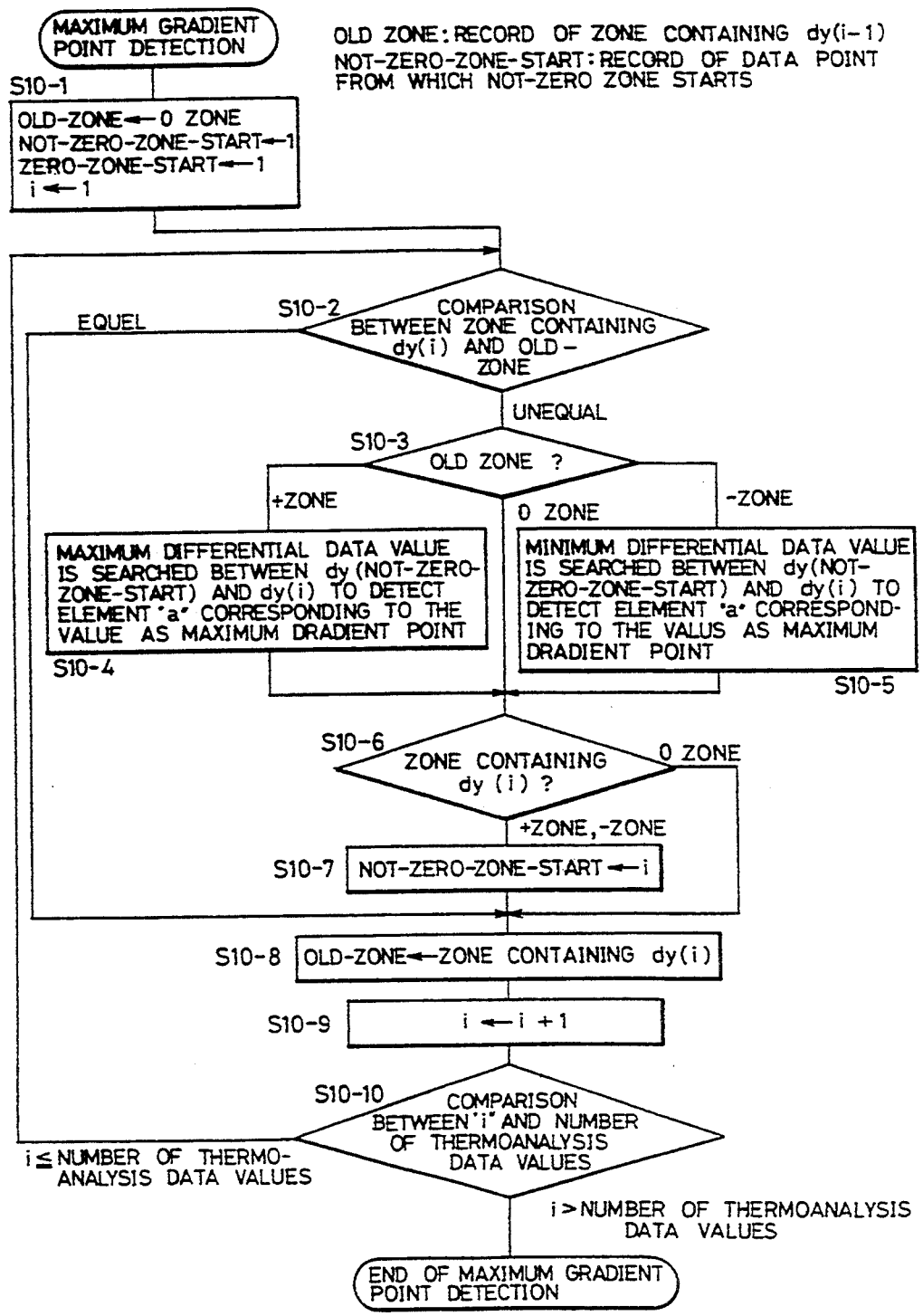
FIG. 10 is a flow chart showing the maximum gradient point detection method of the present invention.

When the stable area detection is completed, the CPU 8 detects the maximum gradient point according to the operation shown by the flow chart in FIG. 10. The operation is described below with reference to FIGS. 10 and 11.

Figure 11A:
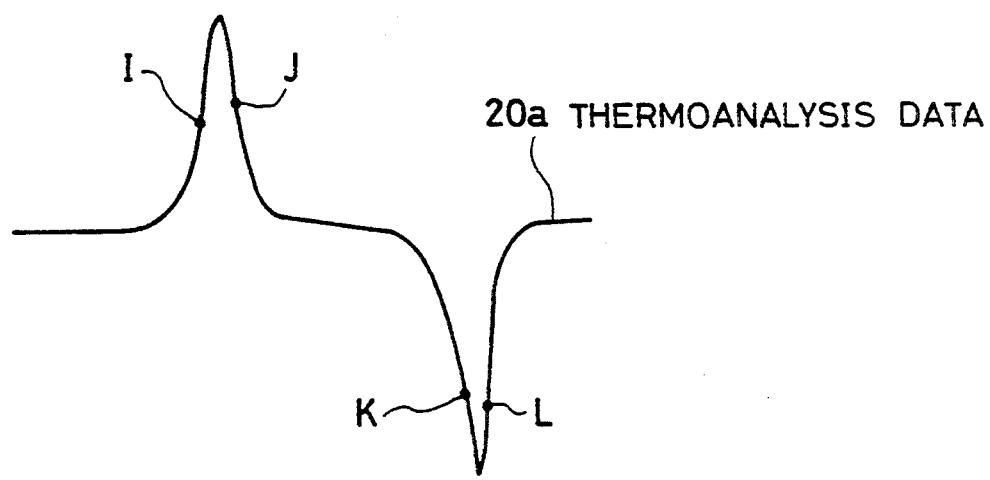
FIGS. 11(a) and 11(b) are explanatory views of the maximum gradient point detection method of the present invention.
Figure 11B:
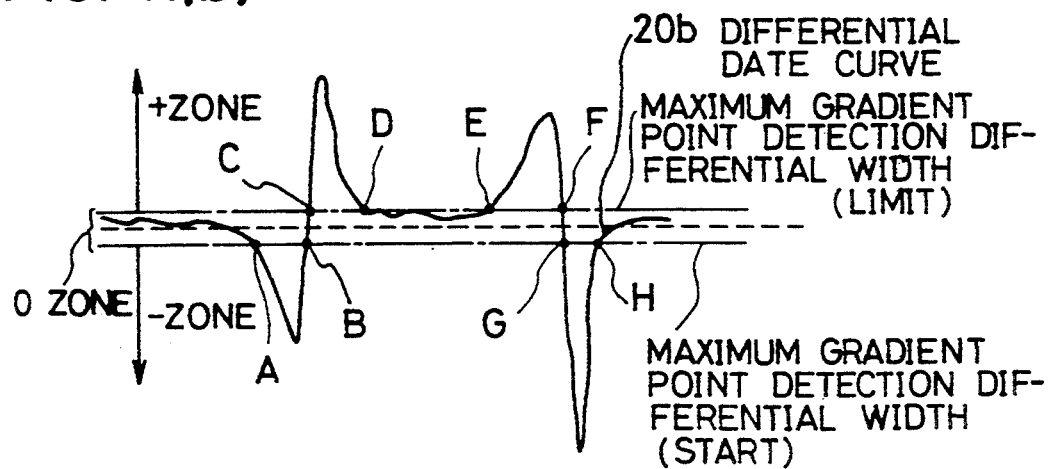
Figure 12:
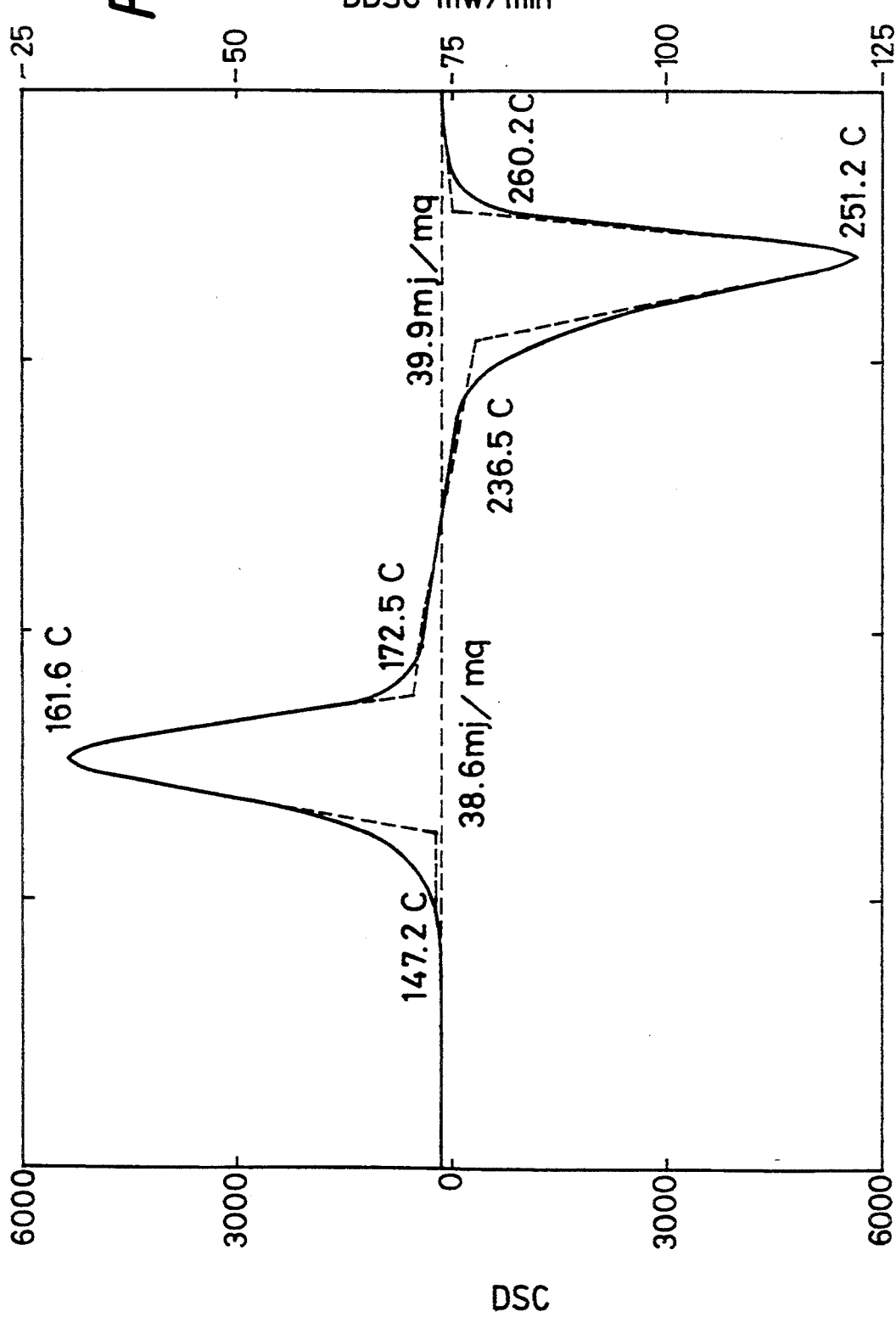
FIG. 12 is an example of a graphic output by the plotter of the embodiment of FIG. 1.

The CPU 8 scans the differential data to detect the maximum gradient point. As shown in FIG. 11(b), the differential data exist in three zones divided by the maximum gradient point differential width [start] and the maximum gradient point differential width [limit] stored in the detection level memory 11. It is assumed that values larger than the maximum gradient point differential width [limit] are in the + zone, those between below the maximum gradient point differential width [limit] and above the maximum gradient point differential width [start] are in the zero zone, and those smaller than the maximum gradient point differential width [start] are in the − zone. In this case, though zone division is performed with two parameters of the maximum gradient point differential width [start] and the maximum gradient differential width [limit], it is also possible to divide the zones into the ± maximum gradient point differential width with zero as the center.

After the initializations of necessary variables are performed (S10-1), each differential data is going to be checked. The zone of the differential data of the point to be currently noticed is checked if there is a change of zone between the point to be currently noticed and point for the differential data one ahead (S10-2).

If there is a change, the zone in which the differential data one ahead was found is checked (S10-3). If the zone of the differential data one ahead was the + zone, it is considered as the point returned from the + zone to the zero zone (e.g. point D in FIG. 11(b)) and the thermal analysis data point (e.g. point J in FIG. 11(a)) corresponding to the maximum differential data between the non-zero zone starting point (e.g. point C in FIG. 11(b)) and the point to be currently noticed is detected as the maximum gradient point with a negative gradient (S10-4). If the zone of the differential data point one ahead is the − zone, it is considered as the point returned from the − zone to the zero zone (e.g. point B in FIG. 11(b)) and the thermal analysis data point (e.g. point I in FIG. 11(a)) corresponding to the minimum differential data between the non-zero zone starting point (e.g. point A in FIG. 11(b)), and the point to be currently-noticed is detected as the maximum gradient point with a positive gradient (S10-5).

When the processes of S10-3 to S10-5 are completed, the zone of the differential data of the point to be currently noticed is checked (S10-6). If the zone of the differential data of the point to be currently noticed is not the zero zone, the point is recorded as the non-zero zone starting point (S10-7). When the processes from S10-2 to S10-7 are completed, by using the processes in which the zone of the point to be currently-noticed is stored as the zone one ahead (S10-8), the point to be noticed is advanced by one (S109) and the comparison is performed between the value of i and the number of thermal analysis data (S10-10), the maximum point is detected.

As described above, in this embodiment the maximum gradient point is determined by scanning differential data. However, there is also a method for determining the peak of differential data by scanning double differential data (like the case in which the peak of thermal analysis data is determined from differential data).

When the detection of the peak point, stable areas, and the maximum gradient point are completed, the CPU 8 computes the transition point and heat of transition.

For computation of transition point, the tracing is performed in two directions of the X-axis, the measurement starting direction and the measurement finishing direction, from the detected peak point to search the nearest maximum gradient point and the center point of the nearest stable area in each direction. The thermal analysis data close to each point is subjected to an approximation linear function to compute the intersection point of two functions as the transition point. This operation is performed for all detected peak points. This embodiment has used the above method. However, it is also possible to perform the function approximation in an entire stable area or to perform a higher-order function approximation.

For computation of the heat of transition point, the tracing is performed in two directions of the X-axis, the measurement start direction and the measurement finishing direction from the detected peak point to search the center point of the nearest stable area in each direction. The heat of transition point is computed by using the method specified in JIS K 7122 based on the two points of the measurement starting direction and the measurement finishing end direction.

A user is free to inquire whether the computed or detected transition point, heat of transition, peak point, stable area, and maximum gradient point are valid or not by using the CRT 7 and keyboard 10. When the inquiry is performed, it is possible to cancel or correct the computed or detected points by using a graphic cursor and the like. In this case, the graphic cursor moves between the detected peak point, stable area, and maximum gradient point.

After computing the transition point and heat of transition, the CPU 8 outputs the transition point, heat of transition, peak point, and thermal analysis data to the CRT 7, printer 1a, or plotter 1b as a graphic (FIG. 12) or as numerical information (FIG. 13).

As described above, in this embodiment the processes such as differential data computation, peak point detection, secondary differential data computation, stable area detection, maximum gradient point detection, transition point computation, and heat-of-transition computation are performed in order. However, it is also possible to perform these processes in parallel according to the result to be determined and the like. For example, when only peak point detection is necessary, peak point detection is performed by one program while computing differential data. Thereby, only peak point detection can be made without using differential data memory and a the like.

As described above, the present invention makes it possible to realize power saving and time saving when many data points are involved, and to improve the reproduceability and uniformity of analysis results, because the peak point, transition point, and heat of transition of thermal analysis data are computed by an apparatus for thermal analysis under a constant processing condition. The present invention also makes it possible to automatically analyze a variety of data with an apparatus for thermal analysis by adding a function for changing detection conditions.

This application relates to subject matter disclosed in Japanese Application number 4-131075, filed on May 22, 1992, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A thermoanalysis arrangement comprising:
   temperature control and measuring means for varying the temperature of a sample while measuring values of a characteristic of the sample, which values change in dependence on changes of the sample temperature such that the characteristic values as a function of sample temperature are representable by a first curve having at least one peak characteristic value;
   a first data memory connected to said temperature control and measuring means for storing the measured characteristic values and associated sample temperature values;
   differentiating means connected to said first data memory for computing a plurality of differential data values by differentiating the stored characteristic values with respect to the stored associated sample temperature values;
   a differentiated data memory connected to said differentiating means for storing the computed differential data values;
   point detecting means connected to said differential data memory for detecting a point on a second curve, representing the stored differential data values as a function of the associated sample temperature values, which point is within a preselected range of differential data values and corresponds to at least one peak characteristic value; and
   output means connected to said point detecting means for outputting an identification of the detected point.

2. A thermoanalysis arrangement according to claim 1 further comprising:
   means for detecting stable areas of the second curve over which the differential data values are substantially constant;
   means for detecting a point of the second curve at which the second curve has a maximum gradient;
   means for computing an intersection point between a first approximation linear function of the first curve at a point corresponding to at least a part of a stable area and a second approximation linear function of the first curve at a point corresponding to the maximum gradient point, which intersection point is a transition point;
   means for computing heat of transition between two detected stable areas enclosing the detected point; and
   means for outputting the computed transition point and heat of transition.

3. A thermoanalysis arrangement according to claim 2 further comprising: means for differentiating the differential data values to produce second differential data values; and a second differential data memory for storing the second differential data values, and wherein said means for detecting stable areas detects an area in which points of second differential values within a preset stable area detection second differential width continue as far as over a preset stable area detection length on the second differential data as a stable area.

4. A thermoanalysis arrangement according to claim 3 further comprising means for comparing the thermoanalysis data of the points detected as the stable areas with a preset stable area detection gradient only for stable areas not exceeding the stable area detection gradient as stable areas.

5. A thermoanalysis arrangement according to claim 4 wherein said means for detecting the maximum gradient point comprise: means for detecting the maximum differential data point as the maximum gradient point in an area selected for the maximum gradient point into parts divided with the preset maximum gradient point detection differential width on the differential data curve when the differential data value is larger than the maximum gradient point detection differential width; and means for detecting the minimum differential data point as the maximum gradient point in the area when the differential data value is smaller than the maximum gradient point detection differential width.

6. A thermoanalysis arrangement according to claim 5 further comprising: a heating furnace for heating a sample; a temperature sensor disposed for detecting a temperature representative of the temperature of the sample; a physical quantity sensor disposed for detecting a physical quantity which changes in dependence on a temperature change of the sample; a measuring and control section which is connected to said heating furnace, said temperature sensor, and said physical quantity sensor, for controlling said heating furnace according to a temperature program, and for digitizing temperature signals produced by said temperature sensor and physical quantity signals produced by said physical quantity sensor; and means for storing the data digitized by said measuring and control section in said first data memory.

7. A thermoanalysis arrangement according to claim 6 further comprising: means for inputting respective ones of the peak detection differential width values, one of the stable area detection second differential width values and stable area detection differential width values, stable area detection length values, maximum gradient point detection differential width values, said stable area detection gradient values by a user, wherein the values are changeable; and a detection level memory for storing inputted values.

8. A thermoanalysis arrangement according to claim 3 wherein said means for detecting the maximum gradient point comprise: means for detecting the maximum differential data point as the maximum gradient point in an area selected for the maximum gradient point into parts divided with the preset maximum gradient point detection differential width on the differential data curve when the differential data value is larger than the maximum gradient point detection differential width; and means for detecting the minimum differential data point as the maximum gradient point in the area when the differential data value is smaller than the maximum gradient point detection differential width.

9. A thermoanalysis arrangement according to claim 8 further comprising: a heating furnace for heating a sample; a temperature sensor disposed for detecting a temperature representative of the temperature of the sample; a physical quantity sensor disposed for detecting a physical quantity which changes in dependence on a temperature change of the sample; a measuring and control section which is connected to said heating furnace, said temperature sensor, and said physical quantity sensor, for controlling said heating furnace according to a temperature program, and for digitizing temperature signals produced by said temperature sensor and physical quantity signals produced by said physical quantity sensor; and means for storing the data digitized by said measuring and control section in said first data memory.

10. A thermoanalysis arrangement according to claim 9 further comprising: means for inputting respective ones of the peak detection differential width values, one of the stable area detection second differential width values and stable area detection differential width values, stable area detection length values, maximum gradient point detection differential width values, said stable area detection gradient values by a user, wherein the values are changeable; and a detection level memory for storing inputted values.

11. A thermoanalysis arrangement according to claim 2 where said means for detecting stable areas comprise means for detecting an area in which points of differential values within a preset stable area detection differential width continue as far as over a preset stable area detection length of the differential data as a stable area.

12. A thermoanalysis arrangement according to claim 11 wherein said means for detecting the maximum gradient point comprise: means for detecting the maximum differential data point as the maximum gradient point in an area selected for the maximum gradient point into parts divided with the preset maximum gradient point detection differential width on the differential data curve when the differential data value is larger than the maximum gradient point detection differential width; and means for detecting the minimum differential data point as the maximum gradient point in the area when the differential data value is smaller than the maximum gradient point detection differential width.

13. A thermoanalysis arrangement according to claim 12 further comprising: a heating furnace for heating a sample; a temperature sensor disposed for detecting a temperature representative of the temperature of the sample; a physical quantity sensor disposed for detecting a physical quantity which changes in dependence on a temperature change of the sample; a measuring and control section which is connected to said heating furnace, said temperature sensor, and said physical quantity sensor, for controlling said heating furnace according to a temperature program, and for digitizing temperature signals produced by said temperature sensor and physical quantity signals produced by said physical quantity sensor; and means for storing the data digitized by said measuring and control section in said first data memory.

14. A thermoanalysis arrangement according to claim 13 further comprising: means for inputting respective ones of the peak detection differential width values, one of the stable area detection second differential width values and stable area detection differential width values, stable area detection length values, maximum gradient point detection differential width values, said stable area detection gradient values by a user, wherein the values are changeable; and a detection level memory for storing inputted values.

* * * * *